United States Patent [19]
Bendek et al.

[11] Patent Number: 5,957,896
[45] Date of Patent: Sep. 28, 1999

[54] MEDICATION DELIVERY PEN

[75] Inventors: Antonio A. Bendek, Vernon, N.J.; John E. Burbank, III, Ridgefield, Conn.; Charles L. Bush, Jr., Fairfield, N.J.; Jonathan B. Gabel, Randolph, N.J.; Lucio Giambattista, East Hanover, N.J.; Roger W. Hoeck, Loomis, Nebr.; Malcolm E. Taylor, Pepperell, Mass.

[73] Assignee: Becton, Dickinson and Company, Franklin Lakes, N.J.

[21] Appl. No.: 08/909,376

[22] Filed: Aug. 11, 1997

[51] Int. Cl.$^6$ ........................................ A61M 5/00
[52] U.S. Cl. .................. 604/207; 604/208; 604/211; 604/232; 222/309; 222/326
[58] Field of Search ..................... 604/218, 232, 604/234, 207, 208–211, 223–224, 187, 181, 186, 152; 222/43, 309, 325–327, 390–391, 386, 287, 336, 46–48

[56] References Cited

U.S. PATENT DOCUMENTS

| | | | |
|---|---|---|---|
| 4,710,178 | 12/1987 | Leonard et al. | 604/209 |
| 4,936,833 | 6/1990 | Sams | 604/209 |
| 4,973,318 | 11/1990 | Holm et al. | 604/208 |
| 5,279,585 | 1/1994 | Balkwill | 604/218 |
| 5,611,783 | 3/1997 | Mikkelsen | 604/211 |

*Primary Examiner*—Ronald K. Stright, Jr.
*Attorney, Agent, or Firm*—Alan W. Fiedler

[57] ABSTRACT

An improved medication delivery pen is provided for injecting fluids such as insulin within body tissue. The medication delivery pen includes a mechanism that prevents the removal of a cartridge unless an injector button on the medication pen is in a predefined position, a bayonet attachment and an improved clutch assembly in a dose setting mechanism that provides improved control over the torque necessary to rotate a units counter ring in the medication delivery pen using a dose setting knob.

8 Claims, 14 Drawing Sheets

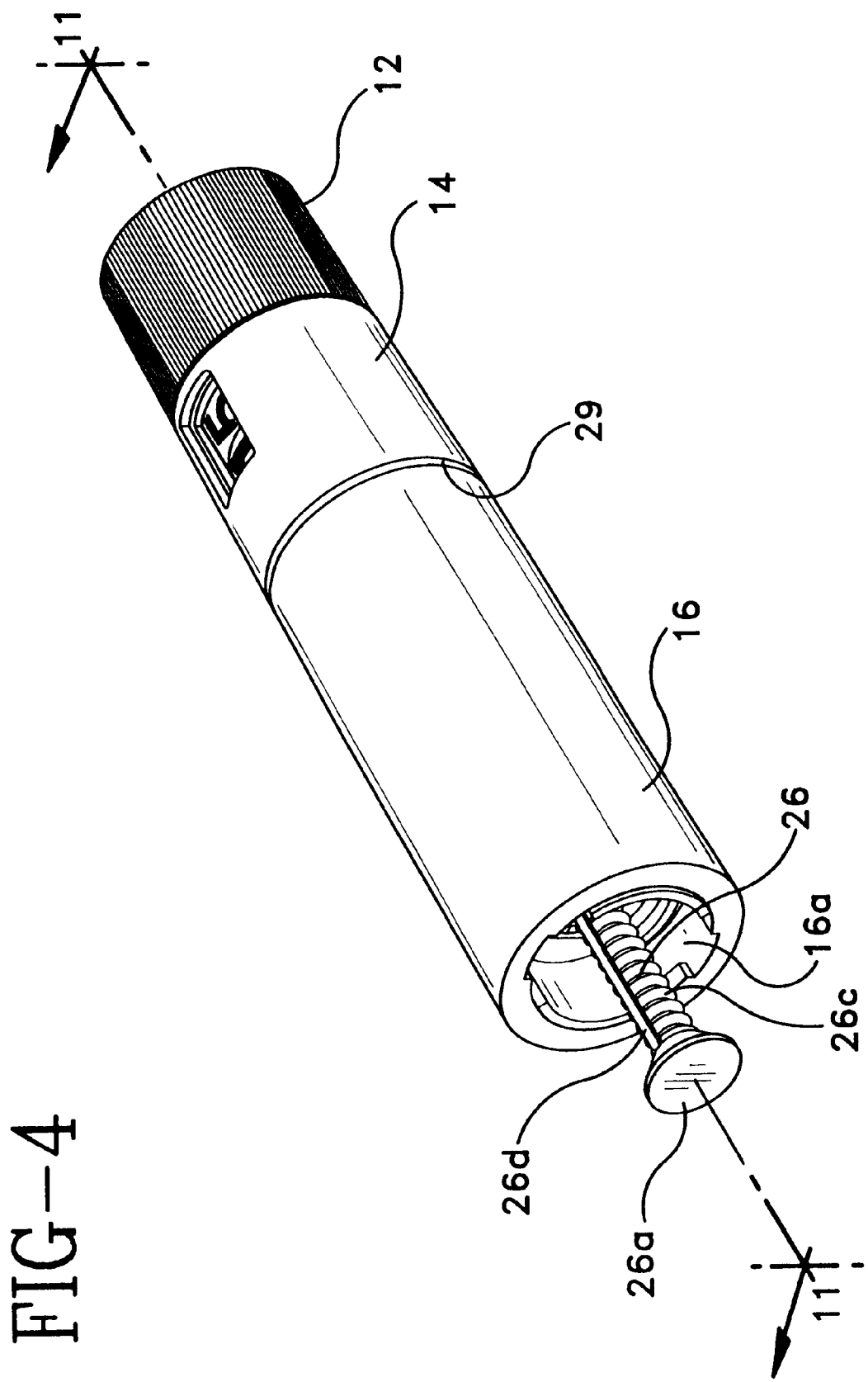

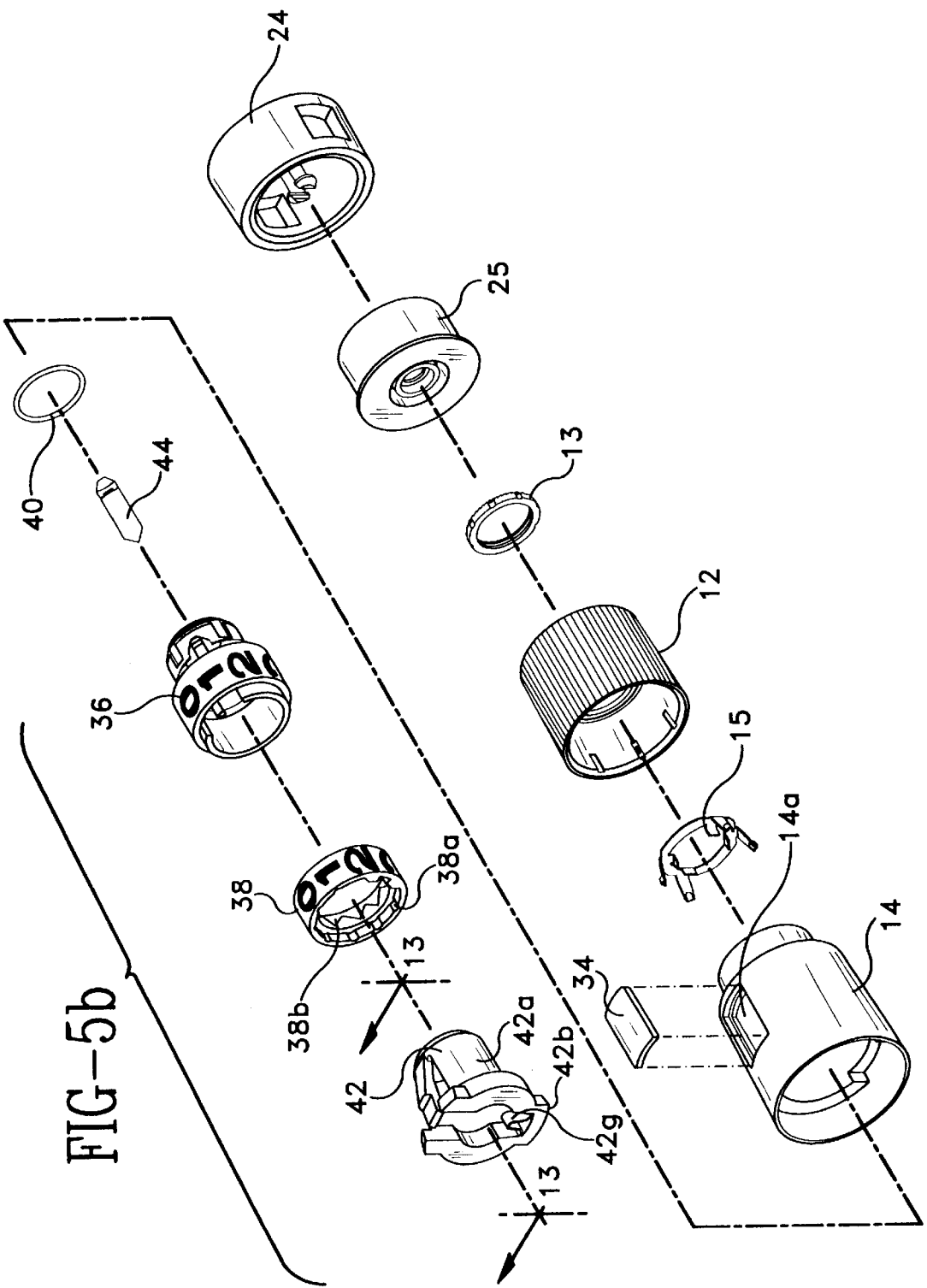

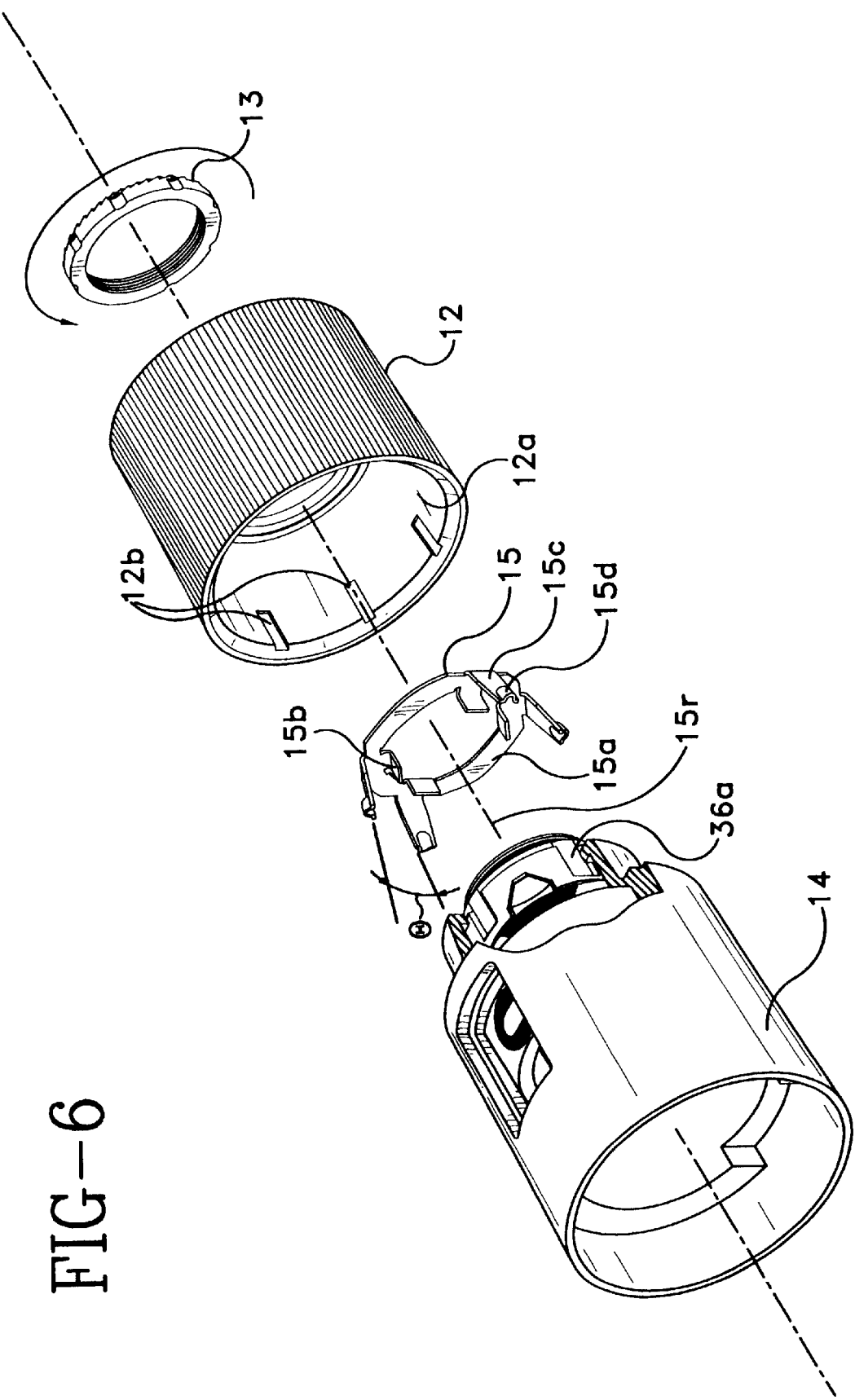

MEDICATION DELIVERY PEN

BACKGROUND OF THE INVENTION

1. Field of the Invention

The subject invention relates to an improved medication delivery pen.

2. Description of Related Art

Hypodermic syringes are used to deliver selected doses of medication to patients. The prior art hypodermic syringe includes a syringe barrel having opposed proximal and distal ends. A cylindrical chamber wall extends between the ends and defines a fluid receiving chamber. The proximal end of the prior art syringe barrel is substantially open and receives a plunger in sliding fluid tight engagement. The distal end of the prior art syringe barrel includes a passage communicating with the chamber. A needle cannula may be mounted to the distal end of the prior art syringe barrel, such that the lumen of the needle cannula communicates with the passage and the chamber of the syringe barrel. Movement of the plunger in a proximal direction draws fluid through the lumen of the needle cannula and into the chamber. Movement of the plunger in a proximal-to-distal direction urges fluid from the chamber and through the lumen of the needle cannula.

Medication to be injected with the prior art hypodermic syringe often is stored in a vial having a pierceable elastomeric seal. Medication in the prior art vial is accessed by piercing the elastomeric seal with the needle cannula. A selected dose of the medication may be drawn into the chamber of the syringe barrel by moving the plunger a selected distance in a proximal direction. The needle cannula may be withdrawn from the vial, and the medication may be injected into a patient by moving the plunger in a distal direction.

Some medication, such as insulin is self-administered. The typical diabetes patient will require injections of insulin several times during the course of a week or day. The required dose of insulin will vary from patient to patient, and for each patient may vary during the course of the day and from day to day. Each diabetes patient will establish a regimen that is appropriate for his or her own medical condition and for his or her lifestyle. The regimen typically includes some combination of a slow or medium acting insulin and a faster acting insulin. Each of these regimens may require the diabetes patient to periodically self-administer insulin in public locations, such as places of employment or restaurants. The required manipulation of the standard prior art hypodermic syringe and vial can be inconvenient and embarrassing in these public environments.

Medication delivery pens have been developed to facilitate the self-administration of medication. One prior art medication delivery pen described in U.S. Pat. No. 5,279,585 includes a vial holder into which a vial of insulin or other medication may be received. The vial holder is an elongate generally tubular structure with proximal and distal ends. The distal end of the prior art vial holder includes mounting means for engaging a double-ended needle cannula. The proximal end also includes mounting means for engaging a driver and dose setting apparatus as explained further below. A disposable vial for use with the prior art vial holder includes a distal end having a pierceable elastomeric seal that can be pierced by one end of a double-ended needle cannula. The proximal end of this prior art vial includes a plunger slidably disposed in fluid tight engagement with the cylindrical wall of the vial. This prior art medication delivery pen is used by inserting the vial of medication into the vial holder. A prior art pen body then is connected to the proximal end of the vial holder. The pen body includes a dose setting apparatus for designating a dose of medication to be delivered by the pen and a driving apparatus for urging the plunger of the vial distally for a distance corresponding to the selected dose.

The user of the pen mounts a prior art double-ended needle cannula to the distal end of the vial holder such that the proximal point cannula of the needle cannula pierces the elastomeric seal on the vial. The user then selects a dose and operates the pen to urge the plunger distally to deliver the selected dose. The user then removes and discards the needle cannula, and keeps the prior art medication delivery pen in a convenient location for the next required medication administration. The medication in the vial will become exhausted after several such administrations of medication. The user then separates the vial holder from the pen body. The empty vial may then be removed and discarded. A new vial can be inserted into the vial holder, and the vial holder and pen body can be reassembled and used again as explained above.

The above described reusable medication delivery pen is effective and much more convenient for self-administration of medication than the typical hypodermic syringe and separate medication vial. However, it has been found that there is the need for additional features and improvements for such a medication delivery pen. For example, there is the need to prevent removal of the vial unless the injector button of the medication delivery pen is in a selected position, to provide improved control over the torques available or necessary to rotate a unit indicator using a dose setting apparatus, and to generally strengthen or otherwise improve the dose setting apparatus in the mediation delivery pen.

SUMMARY OF THE INVENTION

The present invention is directed to providing a medication delivery pen having the features and improvements set forth above.

One object of the present invention is to provide a mechanism in the medication delivery pen that prevents the removal of a vial or cartridge unless the injector button of the medication pen is in a selected position. The feature is provided by using a pair of bayonet connections on the cartridge retainer to activate a locking mechanism in the pen when the cartridge retainer is rotated. In particular, when the injector button is in the up position, the pivot shafts on the half-nuts in the pen prevent rotation of a locking sleeve which prevents removal of the cartridge retainer and cartridge. However, when the injector button is in the down position the pivot shafts on the half nuts in the pen do not prevent rotation of the locking sleeve, which then allows the cartridge retainer to rotate and the bayonet connections to be separated from the pen's housing to remove the cartridge.

Another object of the present invention is to improve the clutch assembly in the medication delivery pen to provide more control over the torques necessary to rotate the unit indicator in the pen using the rotation of a dosing knob in the dose setting apparatus.

A third object of the present invention is to improve the dose dispensing apparatus to provide more definite control over the dose dispensing operation by preventing skewing of the drive mechanism.

These and other aspects, features and advantages of the present invention will become apparent from the following detailed description taken in conjunction with the accompanying drawings.

DESCRIPTION OF THE DRAWINGS

FIG. 4 is a perspective view of the medication delivery pen shown in FIG. 1 with the cartridge retainer removed;

FIGS. 5a and 5b are exploded perspective views of the pen shown in FIG. 1 further including a needle assembly;

FIG. 6 is an enlarged perspective of the clutch assembly;

DETAILED DESCRIPTION

Figure 1:
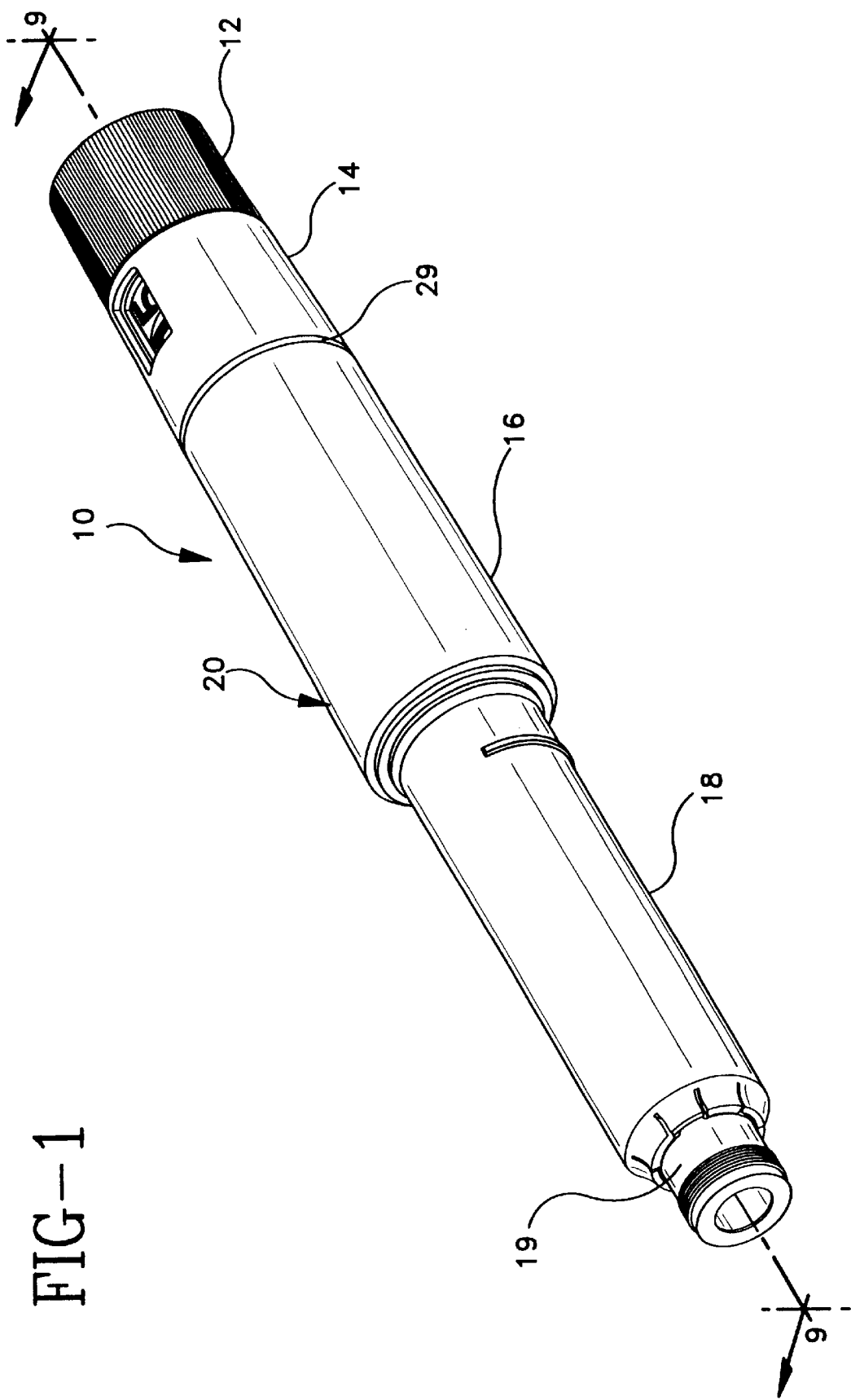
FIG. 1 is a perspective view of a medication delivery pen of the subject invention.
Figure 2:
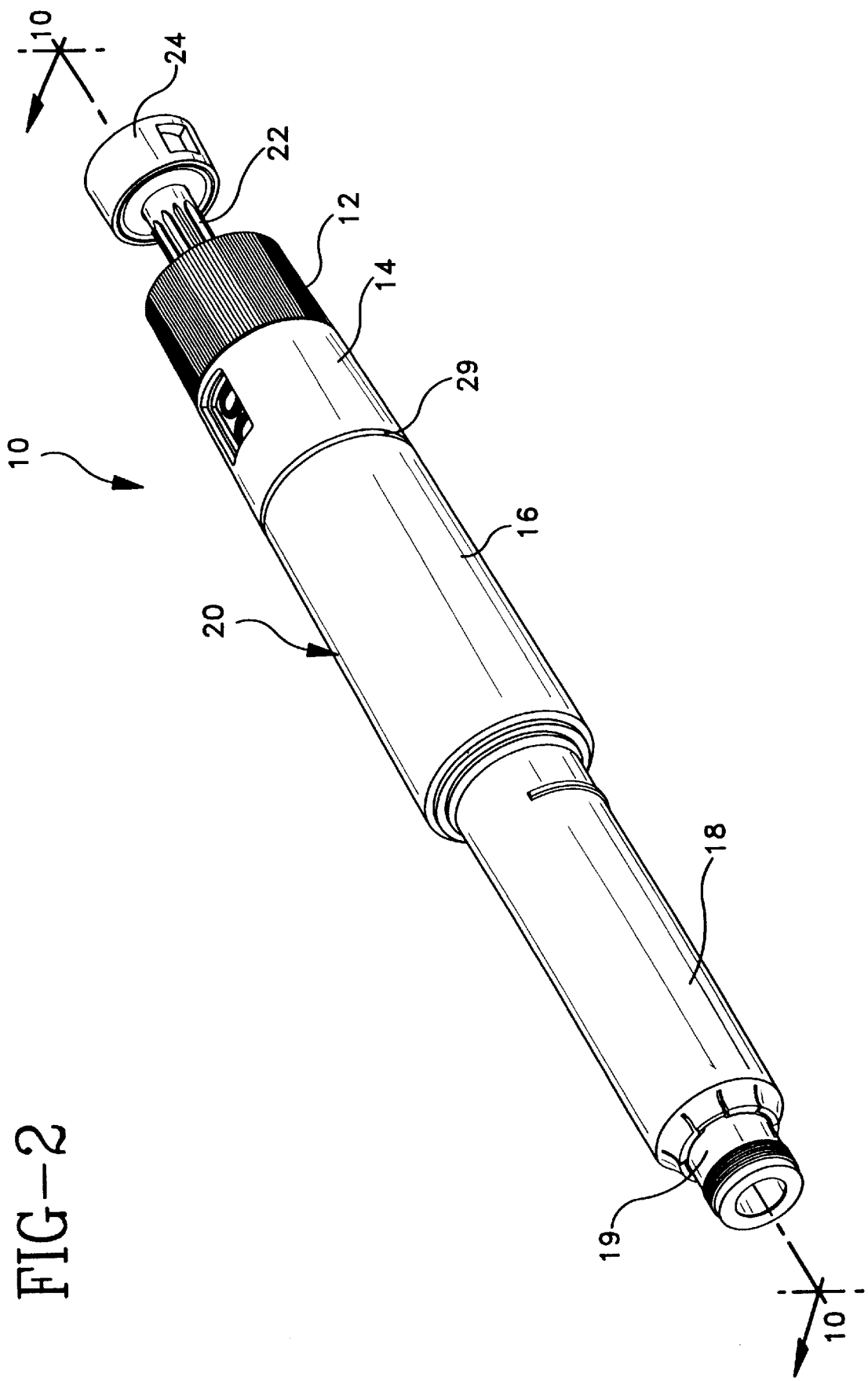
FIG. 2 is a perspective view of the medication delivery pen shown in FIG. 1 with the plunger extended.
Figure 3:
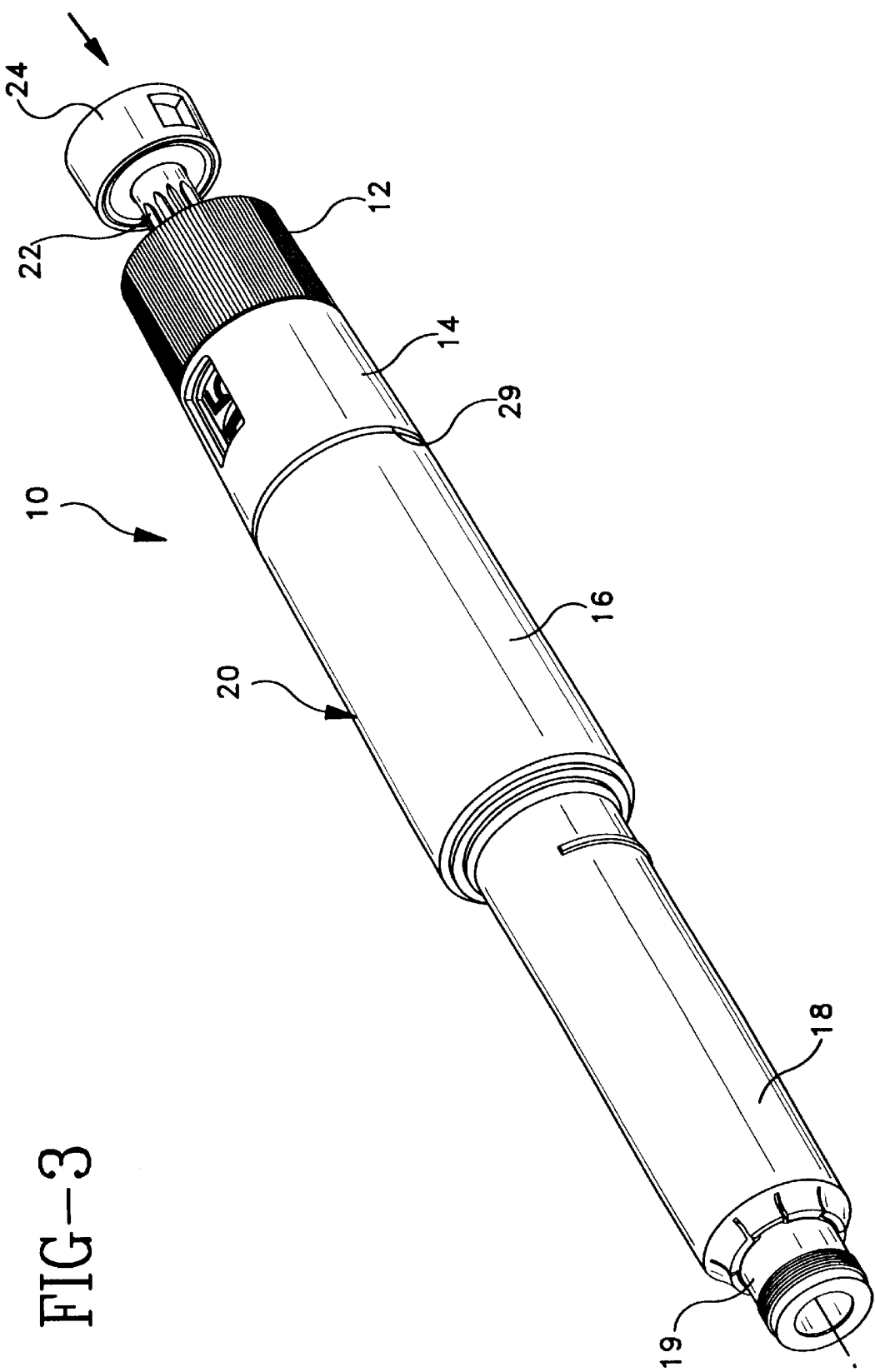
FIG. 3 is a perspective view of the medication delivery pen shown in FIG. 1 with the plunger moving axially during an injection.

An improved injection device 10 for injecting insulin or other medication is provided by the present invention. As shown in FIGS. 1–3, the device includes an adjusting knob 12, an upper body 14, a finishing ring 29, a center body 16, and a cartridge retainer 18 All of these elements have a generally cylindrical configuration and are arranged coaxially to define a generally cylindrical housing 20 which can easily be handled by a patient or medical attendant.

Figure 5A:
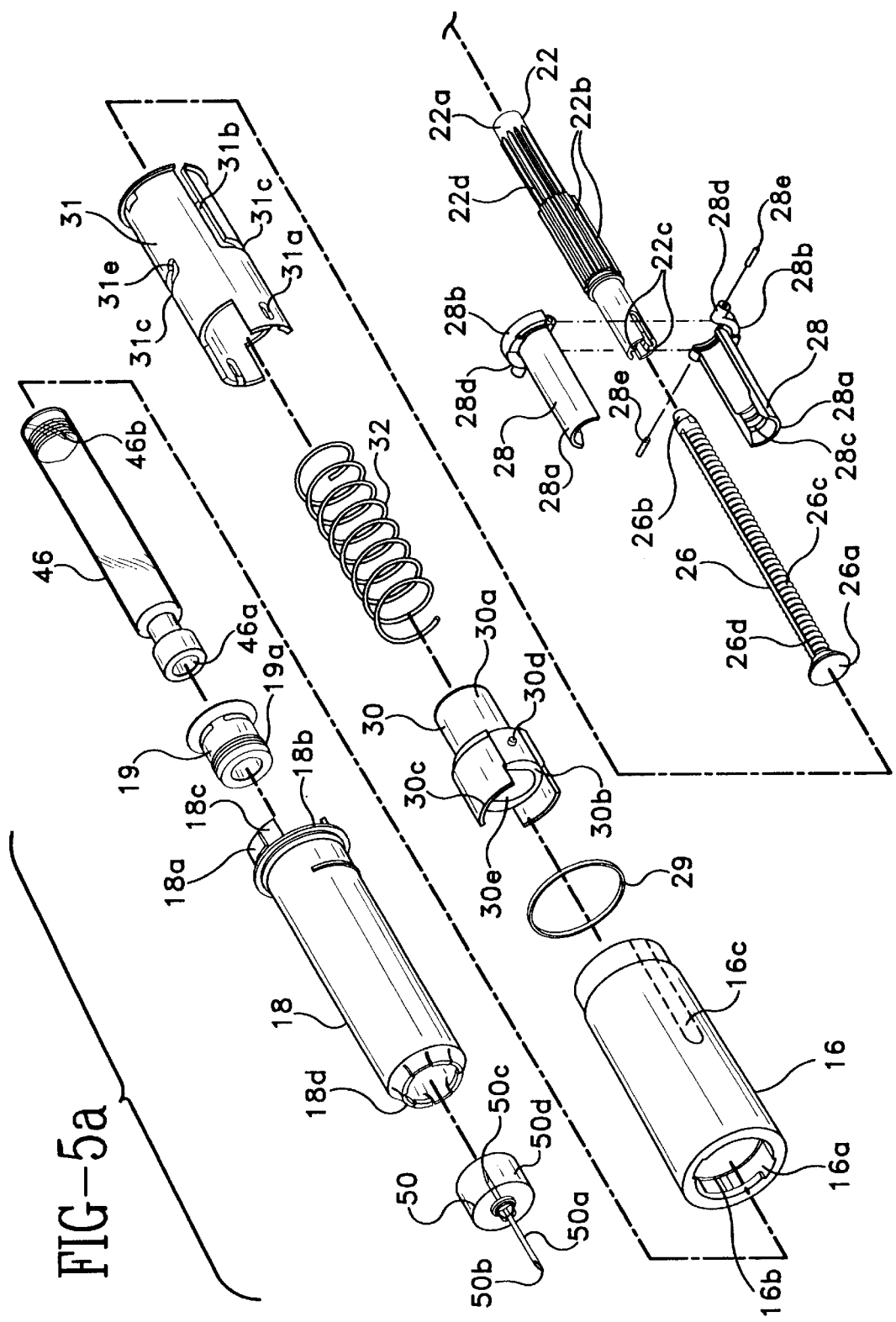

Referring to FIGS. 4, 5a and 7–12, a plunger 22 is at least partially positioned within the portion of housing 20 defined by adjusting knob 12, upper body 14, a finishing ring 29 and center body 16. Plunger 22 includes a hollow, substantially cylindrical body 22a including a band of radially projecting splines 22b extending outwardly therefrom. A pair of opposing projections 22c extend radially inwardly from the front end of the cylindrical body 22a. As shown in FIGS. 5a and 5b, the rear end of plunger 22 is secured to a hub 25 having a rotatable push button 24 snapped therein. Push button 24 fits partially within adjusting knob 12 when plunger 22 is fully inserted within housing 20.

A lead screw 26 is positioned within and coaxially with plunger 22 and includes an enlarged front end 26a and a tapered rear end 26b, connected by an elongate threaded body 26c. A pair of longitudinal grooves 26d are formed within threaded body 26c and receive the radially inwardly extending projections 22c of plunger 22. Lead screw 26 is accordingly rotatable with plunger 22 and capable of sliding axially with respect to plunger 22.

A pair of half-nuts 28 are positioned within center body 16, with each half-nut 28 including a semi-cylindrical body portion 28a and a radially enlarged end portion 28b. The front end of each half-nut 28 includes threads 28c that are used to threadably engage with lead screw 26 and the rear end of each half-nut 28 includes a pivot shaft 28d that receives a metal pin 28e to provide an axis about which each half-nut 28 can pivot. Metal pins 28e inserted in each pivot shaft 28d also provide more definite control over the dose setting operation, described below, and prevent skewing of half nuts 28 on threaded lead screw 26. Body portions 28a of half-nuts 28 are positioned at least partially within a locking ring 30 having a hollow, generally cylindrical body portion 30a defining a generally elliptical passage 30e for receiving half-nuts 28. A front end 30b of locking ring 30 is radially enlarged and includes a pair of angular projections 30c that extend axially from the front end of locking ring 30 and the side of locking ring 30 includes a pair of pins 30d. The proximal end 18b of cartridge retainer 18 includes a pair of angular projections 18c that are spaced to receive angular projections 30c when cartridge retainer 18 is mounted on housing 20, which is described further below.

Figure 9:
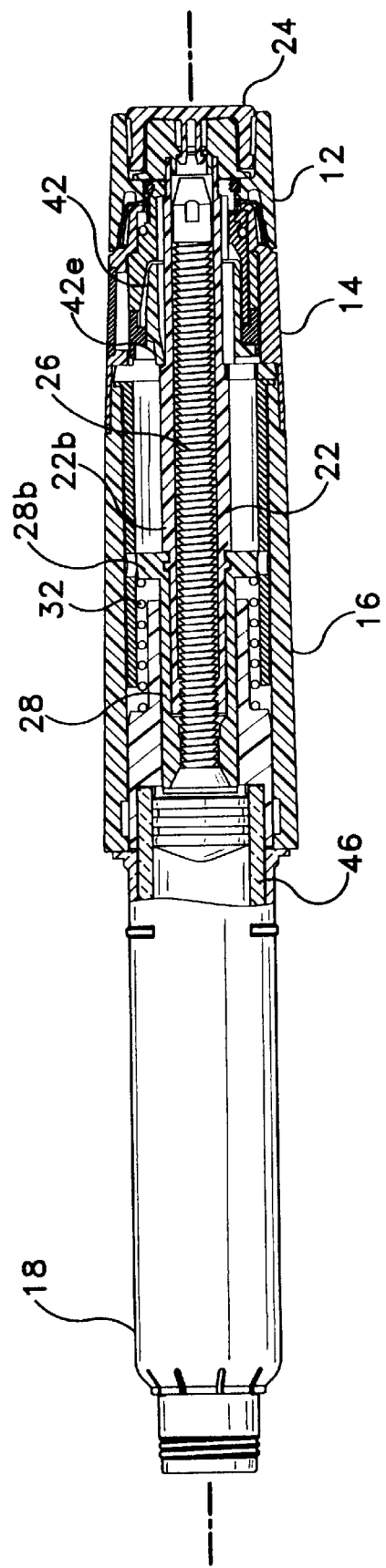
FIG. 9 is a cross sectional view taken along lines 9—9 as shown in FIG. 1.

A helical coil spring 32 is positioned over locking ring 30 and half-nuts 28 and through locking sleeve 31, with one end of coil spring 32 bearing against the radially enlarged portions 28b of half-nuts 28 while the opposite end of coil spring 32 bears against the radially enlarged front end 30b of locking ring 30. Front end 30b of locking ring 30 mounts within center body 16 which also receives finishing ring 29. The rear end portion 28b of half-nuts 28 abut splines 22b of plunger 22, as shown in FIG. 9.

Figure 7:
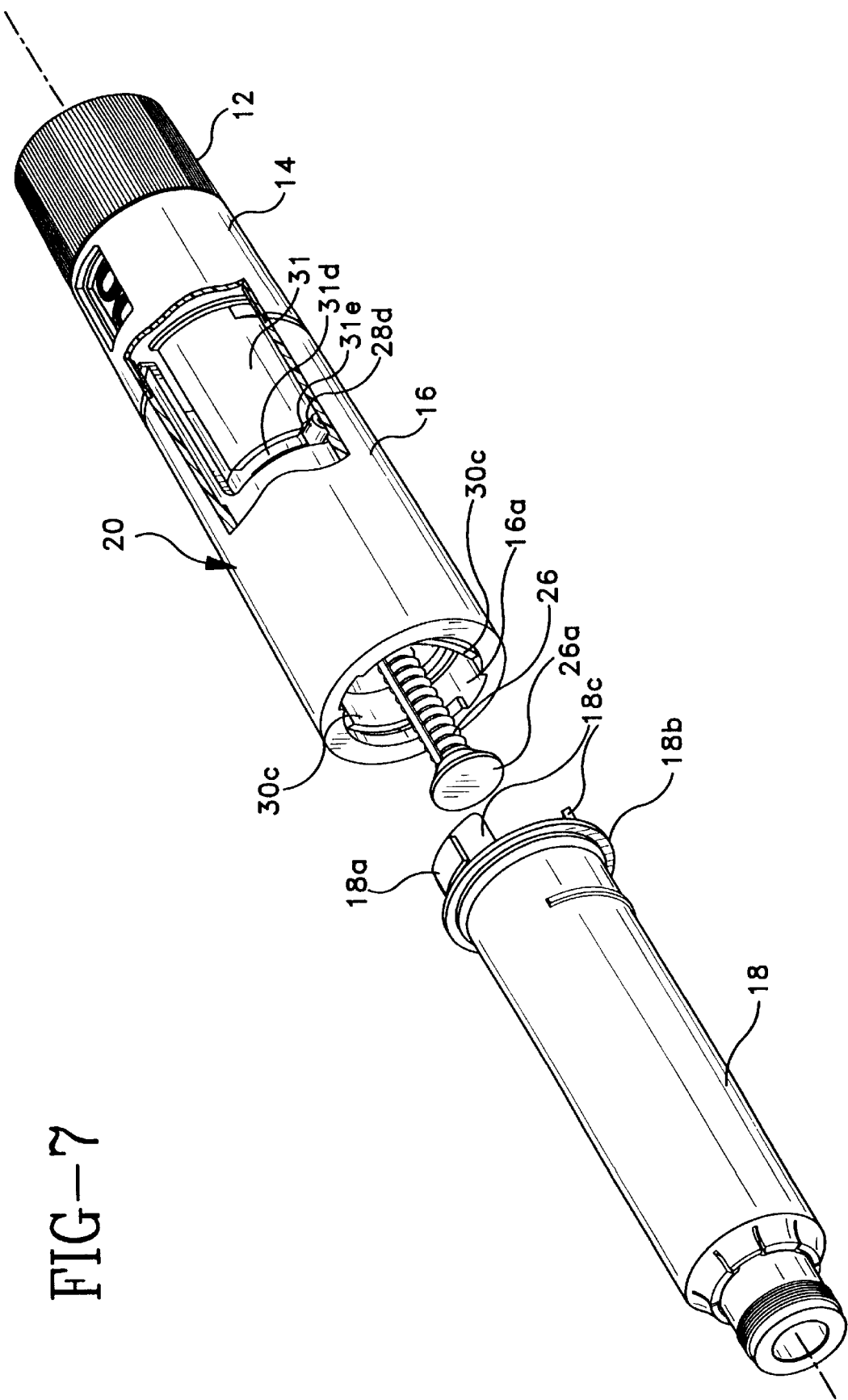
FIG. 7 is an exploded perspective view of the medication delivery pen shown in FIG. 1 with the cartridge retainer removed.
Figure 8:
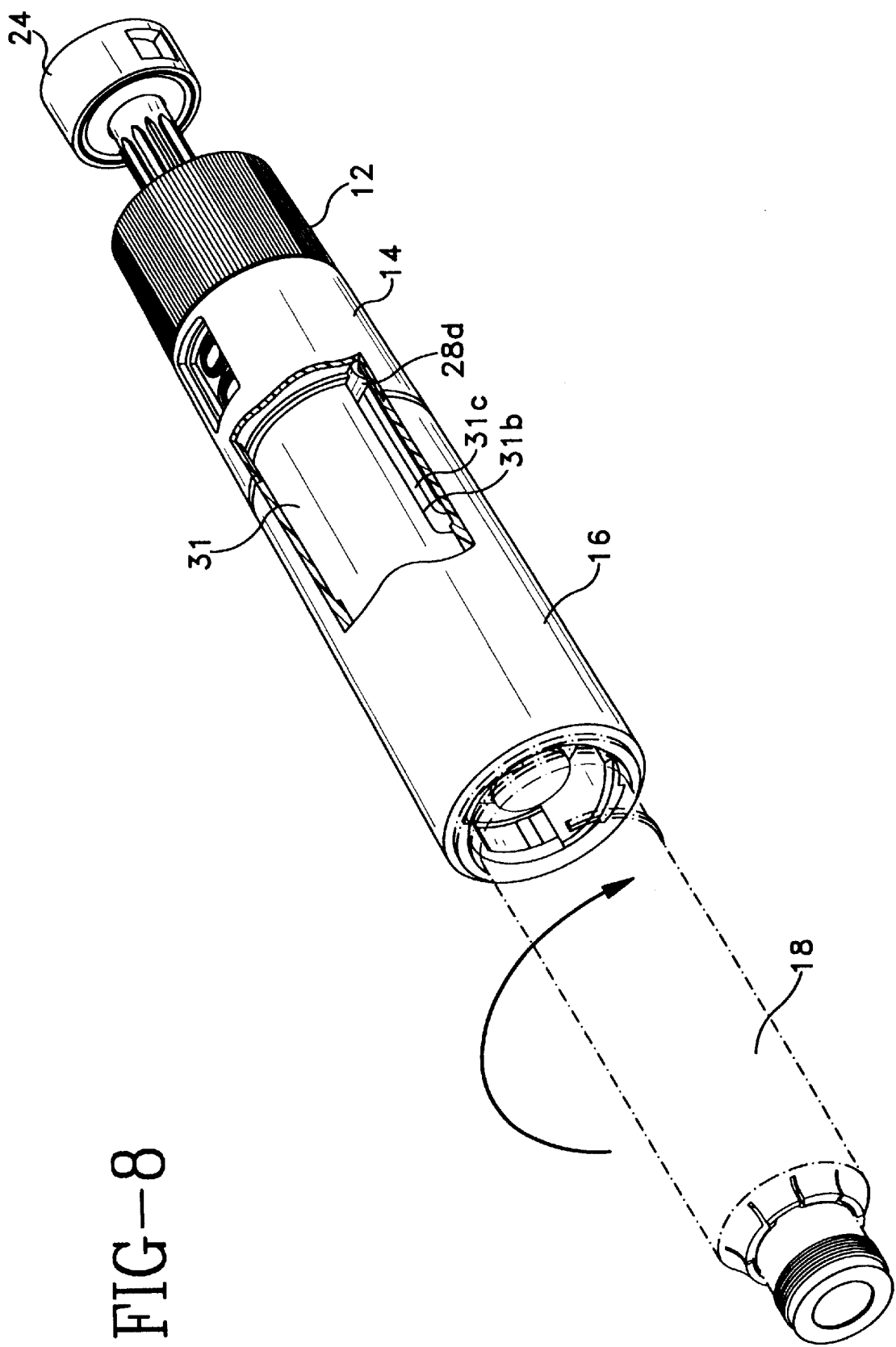
FIG. 8 is another perspective view of the medication delivery pen shown in FIG. 1 with the cartridge retainer attached and locked onto the upper body.

Locking ring 30 is slidably mounted within locking sleeve 31 such that the pair of pins 30d on locking ring 30 are mounted and travel within slot 31a at a distal end of locking sleeve 31. With this structure locking ring 30 is axially movable within locking sleeve 31 but rotates with locking sleeve 31. Locking sleeve 31 also includes a pair of L-shaped grooves 31b and 31c that slidably receive each of the shafts 28d on half-nuts 28. Each pivot shaft 28d in conjunction with its respective L-shaped groove 31b and 31c on locking sleeve 31 and a long groove 16c within center body 16 provides a mechanism that prevents the removal of cartridge retainer 18 and cartridge 46 from housing 20, unless injector button 24 is in a down or loading position. This feature is more clearly shown in FIGS. 7 and 8. In FIG. 7 injector button 24 is in the down or loading position and device 10 is in the proper position for receiving cartridge retainer 18 and, in particular, lugs 18a can enter slot 16a of center body 16. As shown in FIG. 7, locking ring 30 is oriented so that tabs 30c do not block access to slot 16a and in this orientation pivot shafts 28d of half-nuts 28 are located in notches 31e at the end of each lower leg 31d of L-shaped groove 31b. After a cartridge 46 has been loaded into cartridge retainer 18, cartridge retainer 18 is mated with center housing 16 such that lugs 18a enter slot 16a. Then, as shown in FIG. 8, cartridge retainer 18 is rotated in a clockwise direction such that lugs 18a drive tabs 30c in a clockwise direction which moves locking sleeve 31 and causes pivot shaft 28d to slide out of each notch 31e and into each leg 31d of each L-shaped groove 31b and 31c. At this point, spring 32 drives half-nuts 28 in the proximal direction to extend injector button 24 from the proximal end of assembly 10, if dose settings rings 36 and 38 are set to zero.

As shown in FIG. 5b, upper body 14 includes an opening 14a in which a transparent window 34 is mounted. A units counter ring 36 and a tens counter ring 38 are positioned in adjoining relation beneath window 34, with both counter rings 36 and 38 including outer surfaces having numerals thereon visible through window 34.

Figure 12:
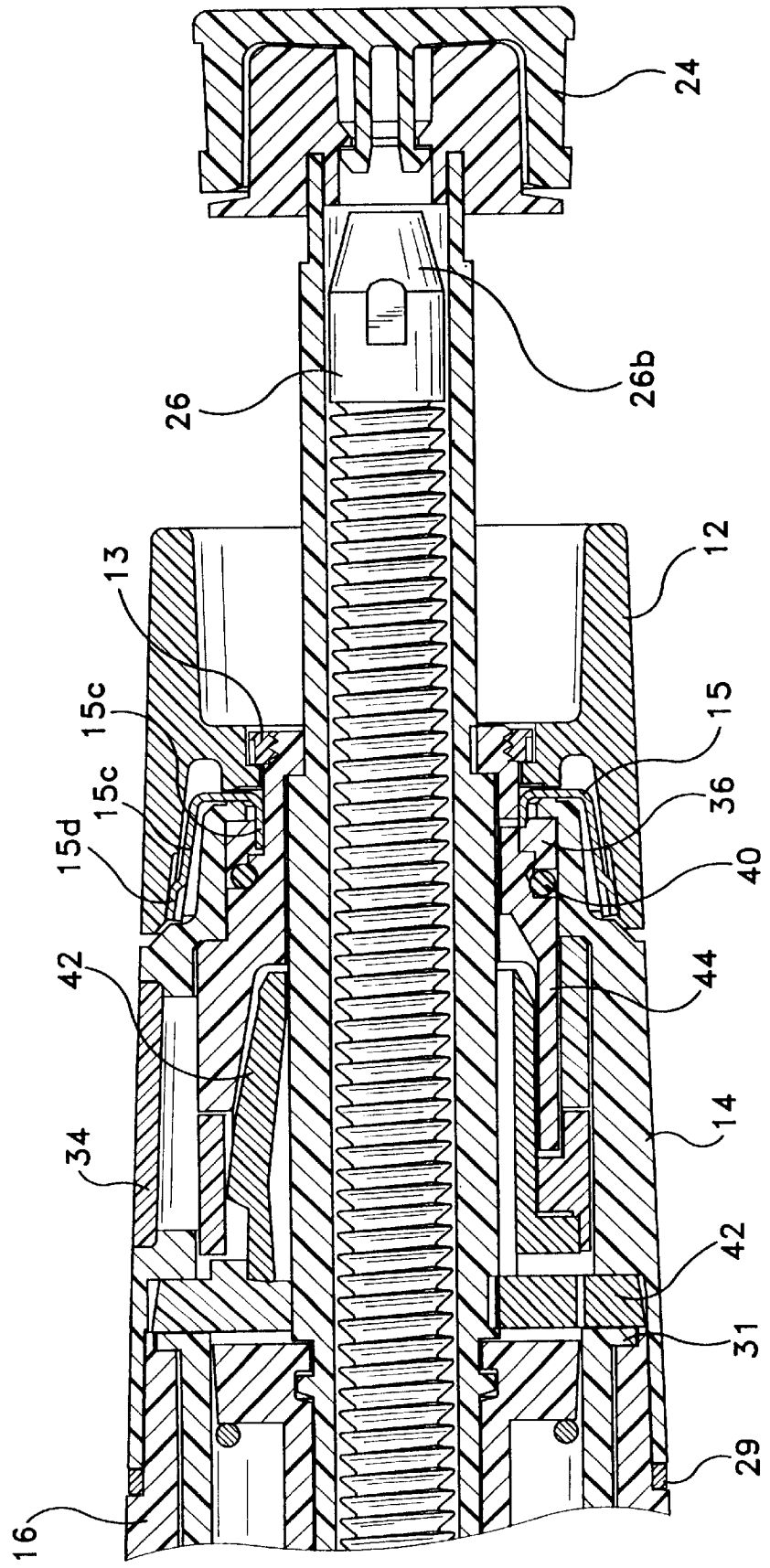
FIG. 12 is an enlarged cross sectional view of the medication delivery pen shown in FIGS. 2 and 10 to more clearly show the clutch assembly.
Figure 14:
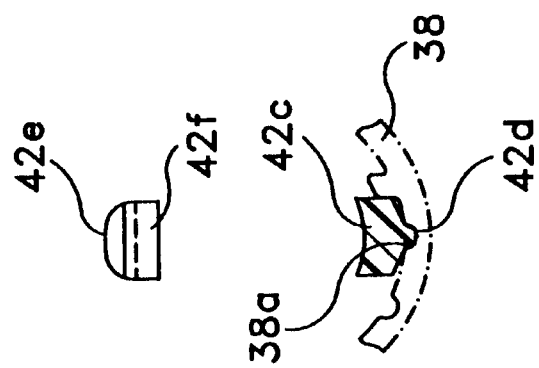
FIG. 14 is a cross sectional view taken along lines 14—14 as shown in FIG. 13.
Figure 13:
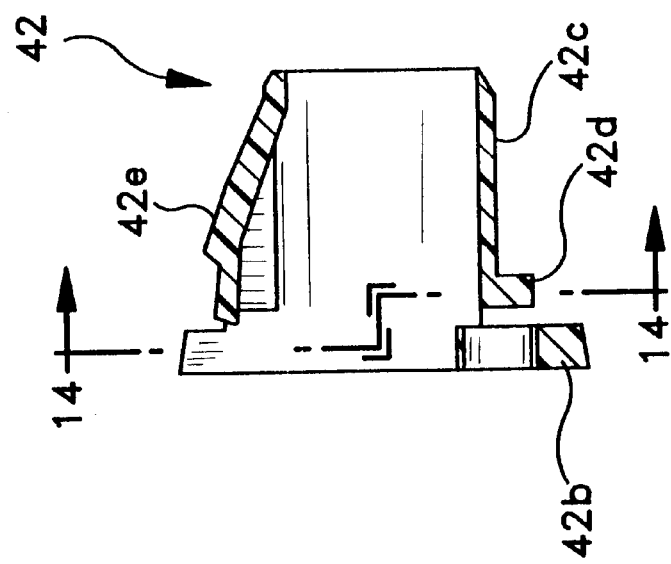
FIG. 13 is an enlarged cross sectional view of the zero detection clip shown in FIG. 5b.

An O-ring 40 made from an elastomeric material is mounted in units counter ring 36 to hold a transmission key 44 in position. Transmission key 44 is provided for engaging and disengaging the units and tens counter rings 36, 38, and is located within a channel formed in units counter ring 36, as shown in FIG. 12. A zero detection clip 42, more clearly shown in FIGS. 13 and 14, is positioned between the inner surfaces of counter rings 36 and 38 and the outer surface of plunger 22. Zero detection clip 42, as shown in FIGS. 5b, 13 and 14, includes a generally cylindrical body 42a having a radially enlarged front end 42b. A lower spring member 42c extends axially within a slot formed within clip body 42a and includes a ridge 42d that is engageable with groove 38a formed within the inner surface of tens counter ring 38, as best shown in FIG. 14. Zero detection clip 42 also includes an axially extending upper spring member 42e, the position of which is controlled by the rotational positions of the units and tens counter rings 36, 38. Upper spring member 42e includes a distal surface 42f that is engageable with splines 22b of plunger 22 when pushed into its active position by units counter ring 36 or by tens counter ring 38. The inner surface of units counter ring 36 functions as a cam and controls the radial position of upper spring member 42e of the zero detection clip 42.

The inner surface of units counter ring 36 is splined, with the spline surface being engageable with small splines 22d of plunger 22. Engagement between ring 36 and plunger 22 occurs when spring 32 is in the extended position shown in FIG. 10. Units counter ring 36 is then driven by adjusting knob 12 through a specially designed clutch detent spring 15, more clearly shown in FIG. 6. Clutch detent spring 15 includes a ring 15a having four internal tabs 15b that mount ring 15a onto units counter ring 36 and four legs 15c that are driven by rotation of adjusting knob 12. The present invention provides a clutch detent spring 15 that is made of a flexible metal that can be manufactured to provide a predetermined slip torque action between adjusting knob 12 and units counter ring 36.

FIG. 6 is an enlarged perspective view of clutch detent spring 15 and shows its connection with adjusting knob 12, clutch nut 13 and units counter ring 36. Clutch detent spring 15 includes ring 15a having four outer legs 15c extending in the distal direction with each leg 15c having a protrusion 15d thereon extending away from rotational axis 15r of clutch detent spring 15. Internal tabs 15b correspond to notches 36a on units counter ring 36 that receive a respective internal tab 15b and hold clutch detent spring 15 onto units counter ring 36 together with the clutch nut 13 that is threaded onto units counter ring 36. When units counter ring 36 with clutch detent spring 15 mounted thereon is assembled into adjusting knob 12, protrusions 15d on clutch detent spring 15 mate with inner surface 12a of adjusting knob 12 and travel in detents 12b on inner surface 12a until a predetermined torque is encountered by units counter ring 36 which then causes clutch detent spring 15 to rotate with respect to adjusting knob 12. The important feature of the present invention is that when the clutch detent spring 15 is manufactured with angle Θ of each outer leg 15c with respect to rotational axis 15r, the clutch detent spring 15 is preset to provide release from adjusting knob 12 at a predetermined torque.

As shown in FIG. 5a, cartridge retainer 18 is adapted for receiving a cartridge 46 of the type including an internal piston 46b and a pierceable seal 46a at one end thereof. A threaded end cap 19 is inserted through cartridge retainer 18 to extend from a distal end 18d of cartridge retainer 18 and is provided with threads 19a for securing a double ended needle assembly 50. The proximal end of cartridge retainer 18 includes the pair of bayonet lugs 18a on angular projections 18c that engage with the pair of slots 16a at the distal end of center body 16.

Needle assembly 50 includes a cannula 50a having a sharp distal end 50b for piercing the skin of a patient or user and a sharp proximal end 50c for piercing pierceable seal 46a of cartridge 46 with a lumen (not shown) therethrough. Needle assembly 50 includes a cup-shaped hub 50d holding cannula 50a so that sharp proximal end 50c projects outwardly from the interior of cup-shaped hub 50d. Cup-shaped hub 50d includes an internal thread that is compatible with thread 19a on end cap 19, so that needle assembly 50 may be removably attached to end cap 19 with its sharp proximal end 50c piercing pierceable seal 46a to establish fluid communication with the interior of cartridge 46.

The operation of the injection device 10 shall now be described with reference to the accompanying figures. Generally speaking, cartridge 46 is loaded within the device, and a double ended needle assembly 50 is affixed to the end of cartridge retainer 18. Fluid communication is accordingly established between the injection portion of double ended needle assembly 50 and the interior of cartridge 46. Once the appropriate dosage is set, push button 24 is urged forwardly, causing lead screw 26 to exert force upon piston 46b movably positioned within cartridge 46. Piston 46b displaces fluid within cartridge 46, causing its injection into body tissue through double ended needle assembly 50. The specific functions which are performed using the injection device are described separately herein. Assuming the device is loaded and push button 24 is in the down position, three steps are followed in the injection procedure: set to zero, set the dose, and make the injection.

First, adjusting knob 12 is rotated back to the zero setting on both counter rings 36 and 38. As will be described in more detail hereinbelow, adjusting knob 12 turns clutch detent spring 15 which then turns units counter ring 36. Because the splines on units counter ring 36 and plunger 22 are disengaged plunger 22 and the lead screw 26 do not turn. When rings 36 and 38 reach zero, their slots align and release upper spring member 42e of zero detection clip 42. This in turn releases plunger 22 and push button 24 which move under pressure from spring 32 via the two half nuts 28 until the proximal ends of large splines 22b of plunger 22 are stopped by an inner surface of units counter ring 36. This movement also carries lead screw 26. Small splines 22d on the plunger 22 engage with the splined units counter ring 36 and are ready for setting a dose.

Adjusting knob 12 is then rotated away from the zero (0) setting. Adjusting knob 12 turns clutch detent spring 15, which turns units counter ring 36, which turns plunger 22. Plunger 22 is engaged with longitudinal grooves 26d in lead screw 26 which turns and screws forward in the nut formed by the two half nuts 28. The lead screw's travel is proportional to the number of units displayed by the counter rings 36, 38.

When the desired dose has been set, push button 24 is pushed fully in which pushes plunger 22, two half nuts 28, and lead screw 26 forwards. Plunger and lead screw 26, as coupled by half nuts 28, accordingly perform the function of a piston rod. The total travel is determined by push button 24 that slides into and is stopped by adjusting knob 12. The first part of the travel brings the end of lead screw 26 into contact with piston 46b of cartridge 46; the second part of the travel moves piston 46b of cartridge 46 forward and delivers the measured amount of medication. While setting the dose, lead screw 26 is moved forward in proportion to the dosage set; this distance determines the proportion of the pre-injection and injection travel. Plunger 22 and push button 24 are locked in position by upper spring member 42e of the zero detection clip 42 following an injection.

When a dose is set, units counter ring 36 pushes upper spring member 42e of zero detection clip 42 into its active position. Zero detection clip 42 includes a clicker 42g that generates a click for each unit as it passes over larger splines 22b on plunger 22. Units counter ring 36 drives the tens counter ring 38 through 36 degrees of rotation every time units counter ring 36 passes zero via transmission key 44. Lower spring member 42e of zero detection clip 42 has a ridge 42d which engages with the grooves 38a inside the tens counter ring 38 and creates a click every time the tens counter ring 38 turns.

If the dose is set at the maximum dialable dose (hereinafter "TMDD"), tens counter ring 38 reaches a stop, and transmission key 44 engages in the last location in the tens counter ring 38. If adjusting knob 12 is turned further, rings 36 and 38 are unable to turn and adjusting knob 12 slips without further effect. Clutch detent spring 15 is designed to limit the torque which will be transmitted to the counter rings and prevents unintentional damage.

The travel of lead screw 26 is limited to the safe travel of piston 46b in the cartridge 46. If lead screw 26 reaches the end of its travel, projections 22c inside plunger 22 reach the end of grooves 26d in lead screw 26 and prevent it from further movement. Lead screw 26 prevents plunger 22 and counter rings 36 and 38 from turning. Adjusting knob 12 will then cause clutch detent spring 15 to slip without further effect. The counter rings will indicate the travel of the lead screw to this point, and therefore, the quantity of insulin remaining in the cartridge.

When adjusting knob 12 is rotated away from the zero (0) setting, and there are more than TMDD units remaining in cartridge 46, the counter rings will stop at TMDD units as described above. If there are less than TMDD units remaining, the counter rings will stop as described above and display the remaining capacity of cartridge 46. In either case, the user can then turn adjusting knob 12 back until the counter rings display the dose to be administered.

Figure 11:
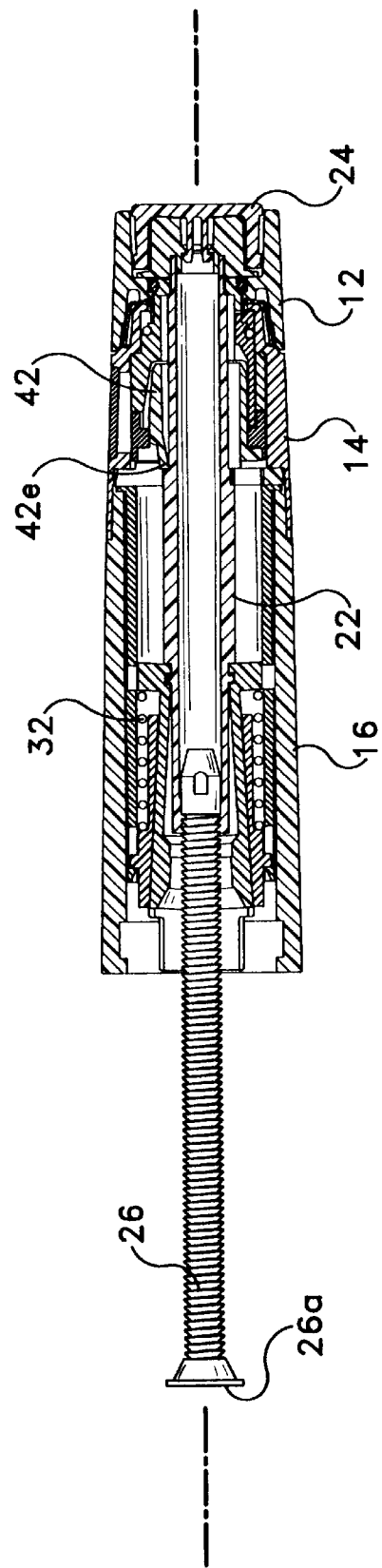
FIG. 11 is a cross sectional view taken along lines 11—11 as shown in FIG. 4.

After a complete injection has been made, push button 24 can be left in the loading position. As described above, when device 10 is in the loading position cartridge retainer 18 can be removed from center body 16 of housing 20 and cartridge 46 can be removed. When cartridge retainer 18 is removed from housing 20, the elliptical shape defined by the inner wall of locking ring 30 allows two half nuts 28 to open under pressure from spring 32 and to free lead screw 26, as shown in FIG. 11.

A new cartridge 46 can then be inserted into cartridge retainer 18 which is then locked back onto center body 16 using the bayonet or lugs 18a on cartridge retainer 18. As cartridge retainer 18 moves towards center body 16, piston 46b of cartridge 46 will push lead screw 26 into the device. Cartridge retainer 18 has two angular projections 18c that engage with angular projections 30c extending from locking ring 30. When cartridge retainer 18 is then rotated the projections 18c and 30c cause locking ring 30 to turn the same amount. In addition, after cartridge retainer 18 has rotated and each lug 18a on cartridge retainer 18 has entered its respective recess 16b in slot 16a inside center body 16, cartridge retainer 18 is prevented from turning further. The elliptical inner wall of locking ring 30 moves two half nuts 28 into engagement with lead screw 26. The position of lead screw 26 is then determined by the position of the piston 46b in cartridge 46.

Upper body 14 houses the four parts which comprise the counter mechanism. Window 34 in upper body 14 shows the numbers printed on the outside of the two counter rings 36 and 38, and indicates the number of units to be injected from 0 to TMDD. Units counter ring 36 is turned by adjusting knob 12 through clutch detent spring 15. When units counter ring 36 has turned to numbered position "8", transmission key 44 meets the cam molded inside upper body 14. The transmission key 44 is then forced to slide up the face of the cam, and reaches the top in position "9". The elastic ring 40 is flexed by this movement and maintains the transmission key 44 in contact with the cam. This movement also brings the opposite end of transmission key 44 into engagement with one of the slots 38b inside the tens counter ring 38, shown in FIG. 5b. When units counter ring 36 is turned further, transmission key 44 transmits the movement to tens counter ring 38, and the two rings turn together. At position "10" the window 34 now displays "10" and transmission key 44 has rotated 36 degrees to the end of the raised face of the cam inside the upper body 14.

If units counter ring 36 is turned further, transmission key 44 is free to slide down the face of the cam inside upper body 14 under pressure from elastic ring 40. This movement disengages the two counter rings, and the counter will now read "11". This movement is repeated each time the units counter ring 36 moves from position "8", through positions "9" and "0" to position "1". The reverse procedure is identical.

The tens counter ring 38 has stops in the "0" and TMDD positions to prevent the counter mechanism from going beyond a maximum reading of TMDD or a minimum reading of 0 units. In both of these positions the transmission key 44 is in its active, engaged position. It should be noted that if the stops for the tens counter ring 38 were moved, the reading could continue up to 99 units.

The slot in units counter ring 36 has an angled face which works as a cam, forcing the upper spring member 42e down into its active position as soon as the units counter ring 36 leaves the "0" position. The units counter ring 36 holds the zero detection clip 42 in its active position up to position "9". In position "10" the tens counter ring 38 has moved, and now holds the zero detection clip 42 in its active position. From position "10" to position TMDD zero detection clip 42 is held in its active position by tens counter ring 38. When an injection is made, plunger 22 slides through the zero detection clip 42 until the end of its travel. At this point the end of upper spring member 42e drops behind the end of spline 22b and prevents plunger 22 from moving out under pressure from spring 32. The components can be designed so that this movement will make a clicking sound, confirming that a complete injection has been made.

Figure 10:
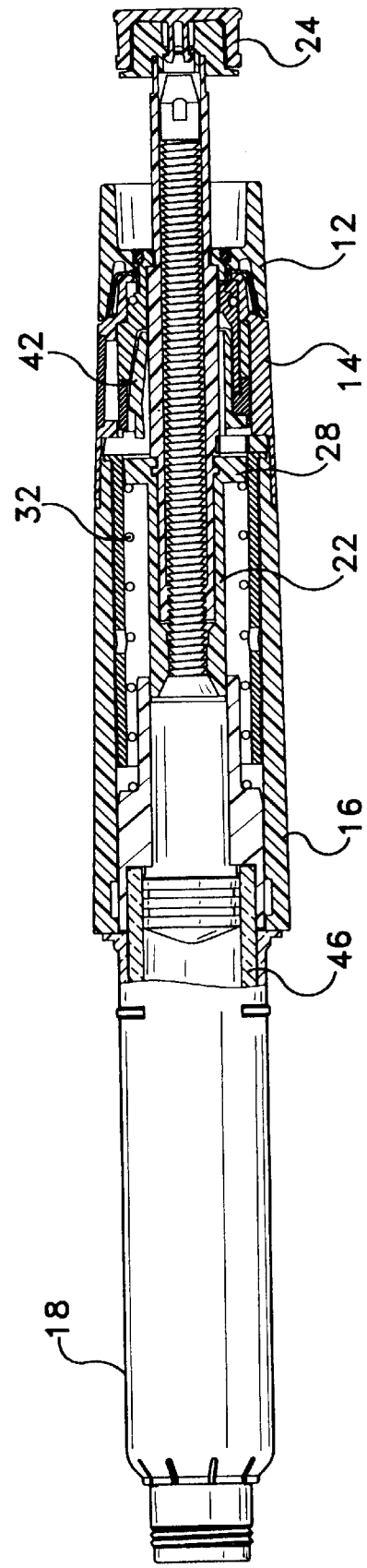
FIG. 10 is a cross sectional view taken along lines 10—10 as shown in FIG. 2.

When the counter is set to "0" as shown in FIG. 10, the slots inside the two counter rings 36 and 38 align with upper spring member 42e of zero detection clip 42 and allow it to spring up into its rest position. This movement frees plunger 22 and allows a new dose to be set.

Cartridge 46 is easily loaded and substantially fully visible to the user. Two way dosage adjustment is possible, which allows corrections to be made quickly and easily. The dosage to be administered is clearly displayed and will remain displayed subsequent to the injection procedure. In order to insure that a complete injection has been made, the device produces a click and locks in the closed position only when the plunger is fully inserted.

While the invention has been described with respect to a preferred embodiment illustrated in FIGS. 1–14, it should be understood that variations from this preferred embodiment may be provided, and are considered to be within the scope of the subject invention.

What is claimed is:

1. A medication delivery pen comprising:

a housing comprising a distal end and a proximal end;

a cartridge retainer for receiving a cartridge containing medication, said cartridge retainer being removably mountable on the distal end of said housing;

means in said housing for setting a desired dose of medication to be dispensed from the cartridge;

means in said housing for dispensing the desired dose of medication from the cartridge, said dispensing means having a loading position for loading and unloading the cartridge from said cartridge retainer and a delivery position for dispensing medication from the cartridge; and means in said housing for preventing the removal of said cartridge retainer from said housing when said dispensing means is in the delivery position, wherein said means for preventing removal of said cartridge retainer from said housing comprises:

a locking sleeve having a distal end and a proximal end having a L-shaped groove;

a locking ring having a pair of tabs extending from a distal end and a proximal end slidably attached to the distal end or said locking sleeve; and a pair of half-nuts having internal threads and connected together at a proximal end by a pivot shaft on each of said half-nuts, said pivot shaft traveling within said L-shaped groove of said locking sleeve as said dispensing means moves from the delivery position to the loading position.

2. A medication delivery pen according to claim 1, further comprising attachment means between said cartridge retainer and said housing for attaching and unattaching said cartridge retainer to said housing, wherein said attaching means is disabled from unattaching said cartridge retainer from said housing by said preventing means when said dispensing means is in said delivery position.

3. A medication delivery pen according to claim 2, wherein said attachment means is a bayonet like attachment between said housing and said cartridge retainer.

4. A medication delivery pen according to claim 3, wherein said bayonet like attachment includes a pair of projections on the proximal end of said cartridge retainer and a pair of slots in the distal end of said housing.

5. A medication delivery pen according to claim 4, wherein movement of said pair of projections on the proximal end of said cartridge retainer in said pair of slots in said housing cause said locking ring and locking sleeve to rotate and said pivot shaft to travel within said L-shaped groove.

6. A medication delivery pen according to claim 1, wherein said dispensing means includes an injector button extending from the proximal end of said housing, said injector button being in an up position when said dispensing means is in the delivery position prior to dispensing medication and in a down position when said dispensing means is in the loading position, whereby said means for preventing removal of said cartridge retainer prevents removal of said cartridge retainer when said injector button is in the up position.

7. A medication delivery pen according to claim 1, wherein said pair of half-nuts are hingably connected together at said pivot shaft on each of said half-nuts by a pair of pins through said pivot shaft.

8. A medication delivery pen comprising:

a housing comprising a distal end and a proximal end;

a cartridge retainer for receiving a cartridge containing medication, said cartridge retainer being removably mountable on the distal end of said housing;

means in said housing for setting a desired dose of medication to be dispensed from the cartridge;

means in said housing for dispensing the desired dose of medication from the cartridge, said dispensing means having a loading position for loading and unloading the cartridge from said cartridge retainer and a delivery position for dispensing medication from the cartridge; and means in said housing for preventing the removal of said cartridge retainer from said housing when said dispensing means is in the delivery position, wherein said dispensing means includes a lead screw having a thread and a pair of half-nuts having internal threads, said half-nuts being hingably connected together at a pivot shaft on each of said half-nuts such that said threads in said half-nuts threadably engage the thread on said lead screw within the medication delivery pen when said dispensing means is in the delivery position and rotate away from the thread on said lead screw when said dispensing means is in the loading position.

* * * * *